(12) United States Patent
Vazifehdan et al.

(10) Patent No.: US 11,471,304 B2
(45) Date of Patent: Oct. 18, 2022

(54) CAGE AND POSITIONING INSTRUMENT FOR A CAGE POSITIONING SYSTEM

(71) Applicant: Premiere Medical GmbH, Erbach (DE)

(72) Inventors: Farzam Vazifehdan, Stuttgart (DE); C. Michael Nilsson, Moreland Hills, OH (US); Helmut Schoenhoeffer, Erbach (DE)

(73) Assignee: Premiere Medical GmbH, Erbach (DE)

( * ) Notice: Subject to any disclaimer, the term of this patent is extended or adjusted under 35 U.S.C. 154(b) by 0 days.

(21) Appl. No.: 16/947,354

(22) Filed: Jul. 29, 2020

(65) Prior Publication Data

US 2020/0352740 A1 Nov. 12, 2020

Related U.S. Application Data

(63) Continuation of application No. PCT/EP2019/052241, filed on Jan. 30, 2019.

(30) Foreign Application Priority Data

Jan. 30, 2018 (DE) ...................... 10 2018 201 399.3

(51) Int. Cl.
*A61F 2/46* (2006.01)
*A61F 2/44* (2006.01)

(52) U.S. Cl.
CPC .......... *A61F 2/4611* (2013.01); *A61F 2/4455* (2013.01); *A61F 2002/4622* (2013.01)

(58) Field of Classification Search
CPC ........ A61F 2/4611; A61F 2/4455; A61F 2/44; A61F 2002/443; A61F 2002/4622
See application file for complete search history.

(56) References Cited

U.S. PATENT DOCUMENTS

| | | | | |
|---|---|---|---|---|
| 2004/0153065 | A1* | 8/2004 | Lim | ...................... A61F 2/4465 606/53 |
| 2006/0235426 | A1 | 10/2006 | Lim et al. | |
| 2008/0109005 | A1* | 5/2008 | Trudeau | .................. A61F 2/442 606/99 |

(Continued)

FOREIGN PATENT DOCUMENTS

WO 2008 121251 A2 10/2008

*Primary Examiner* — Matthew J Lawson
(74) *Attorney, Agent, or Firm* — Hackler Daghighian Martino & Novak

(57) ABSTRACT

A surgical cage positioning system for the implantological replacement of an intervertebral disk, in the region of the lumbar spine of humans, has a positioning instrument with a first coupling prong and with a first manipulator prong, each provided with a coupling element. The manipulator prong can be displaced in the axial direction relative to the coupling prong by means of a handle. The cage positioning system has a cage with an insertion opening for the instrumentation segment and with coupling means, via which the coupling elements of the instrumentation segment, each pivotally connected to the cage, can be coupled so that the cage can be pivoted by means of the manipulator prong about an axis of rotation defined by the coupling element of the coupling prong and the coupling means of the cage relative to the longitudinal axis of the positioning instrument.

17 Claims, 15 Drawing Sheets

(56) References Cited

U.S. PATENT DOCUMENTS

| | | |
|---|---|---|
| 2008/0140085 A1 | 6/2008 | Gately et al. |
| 2008/0154377 A1* | 6/2008 | Voellmicke ............. A61F 2/447 623/17.16 |
| 2010/0094422 A1 | 4/2010 | Hansell et al. |
| 2012/0265211 A1* | 10/2012 | Lim ...................... A61F 2/4611 606/99 |
| 2013/0297026 A1 | 11/2013 | de Villiers et al. |

* cited by examiner

CAGE AND POSITIONING INSTRUMENT FOR A CAGE POSITIONING SYSTEM

CROSS-REFERENCE TO RELATED APPLICATIONS

This continuation application claims priority to PCT/EP2019/052241 filed on Jan. 30, 2019 which has published as WO 2019/149749 A1 and also the German application number 10 2018 201 399.3 filed on Jan. 30, 2018, the entire contents of which are fully incorporated herein with these references.

DESCRIPTION

Field of the Invention

The invention relates to a cage positioning system, to a cage, and to a positioning instrument for such a cage positioning system.

Background of the Invention

In the case of traumatic and/or degenerative diseases of the lumbar spine, an intervertebral fusion of vertebral bodies is often carried out to correct and stabilize the spine. For this purpose, the damaged intervertebral disk is removed and replaced by means of an intervertebral disk space holder, the so-called cage, to be implanted in its intervertebral disk space. The vertebrae adjacent to the intervertebral disk space are stabilized relative to each other by a fixateur internet during a transpedicular approach to the spinal column. The stabilizing effect can optionally be further ensured by a metal plate screwed onto the vertebral body from the front—a so-called ventral plate osteosynthesis. Among spinal reinforcement interventions, so-called "PLIF" (posterior lumbar interbody fusion), "ALIF" (anterior lumbar interbody fusion) and "TLIF" ("transforaminal lumbar interbody fusion") are differentiated depending on the respective surgical access route.

The implanted cage, which is usually made of titanium, usually grows integrally into the adjacent vertebral bodies within six to twelve weeks. Before the actual operation, the specific amount of correction required for an individual, i.e. the given height and angle of the intervertebral disk space and thus the position of the vertebrae bordering the intervertebral disk space, is usually determined using imaging methods. As soon as the operated spine section is stable in a certain position, the other spine areas are inevitably moved and loaded differently, which can lead to signs of wear over time. This is particularly the case if the implanted cage has fixed the vertebrae in a suboptimal position or has itself been incorrectly positioned.

Today's surgical procedures are rather risky due to unavoidable preoperative measurement and calculation errors and, in particular, also intraoperative difficulties in positioning the cage in the correct position and orientation in the intervertebral disk compartment. The cage implants available on the market must also be stocked in a sufficient number of variants in order to even partially meet individual requirements for the angle and height adjustment of the intervertebral disk compartment.

It is therefore the object of the present invention to provide a cage positioning system with which a cage to be implanted can be positioned in the individually correct position and orientation in the prespecified intervertebral disk compartment in a simplified, safer, less traumatic and more controlled manner. The cage positioning system should, if possible, meet the patient's individual anatomical requirements more universally.

SUMMARY OF THE INVENTION

The object relating to the cage positioning system is achieved by a cage positioning system having the features specified in the first independent claim 1. The cage and the positioning instrument have additional features specified in the dependent claims.

The surgical cage positioning system is used for the replacement of an intervertebral disk using an implant, preferably in the area of the lumbar spine of humans. The cage positioning system comprises a positioning instrument having an actuating segment and having an instrumentation segment which extends away from the actuating segment in the direction of the longitudinal axis of the positioning instrument. The instrumentation segment has a first coupling prong and a first manipulator prong, each of which has a coupling element on its free end section. The manipulator prong is displaceable in an axial direction (back and forth) relative to the coupling prong by means of a handle which is preferably arranged on the actuating segment of the positioning instrument.

The cage positioning system further comprises a cage to be implanted as an intervertebral disk replacement, having an insertion opening for the instrumentation segment and having coupling means via which the coupling elements of the instrumentation segment can each be pivotally coupled to the cage. The coupling means and the coupling elements of the positioning instrument coupled to the cage work together in such a way that the cage can be pivoted by means of the manipulator prong relative to the longitudinal axis of the positioning instrument about a first axis of rotation defined by the coupling element of the coupling prong and the coupling means of the cage.

By means of the cage positioning system according to the invention, the cage can be inserted into the operation site, and into the intervertebral disk compartment provided for receiving the cage, in the direction of its transverse axis, along which the cage generally has its greatest extent, and can be transferred into its prespecified rotational position relative to the adjacent vertebral bodies once in the intervertebral disk compartment. The reversible connection of the manipulator prong to the cage means that the surgeon always has complete control over the respective pivot angle of the cage relative to the positioning instrument. As a result, the cage can be positioned and placed overall in a simpler, quicker, more non-traumatic and more precise manner at a prespecified position and in a prespecified orientation in the intervertebral disk compartment. In the long term, this can also counteract undesirable signs of wear and incorrect posture of the spine as a result of the surgical intervention, in particular due to the suboptimal positioning of the cage in the intervertebral disk compartment.

According to a particularly preferred development of the invention, the coupling means of the cage assigned to the coupling element of the manipulator prong causes a translational displacement of the coupling element of the manipulator prongs along a non-linear movement path relative to the cage when the cage is pivoted. As a result, the cage can be pivoted in the intervertebral disk compartment over a sufficiently large pivot angle relative to the coupling prong or the longitudinal axis of the positioning instrument.

The coupling means of the cage corresponding to the coupling element of the manipulator prong can, according to the invention, be designed in particular as a non-linear depression of the cage in the form of a non-linear groove or a non-linear elongated hole. When pivoting, the elongated hole acts as a control link for the other coupling element of the manipulator prong which engages therein.

It goes without saying that the insertion opening of the cage must be designed for a prespecified maximum pivot angle in each case. In cases where it should be possible to orient the transverse axis of the cage on the positioning instrument parallel or substantially parallel to the longitudinal axis of the positioning instrument, the insertion opening can advantageously be designed to be open towards the lateral surface of the cage.

According to the invention, the cage coupled to the instrumentation segment of the positioning instrument can be pivoted (rotated) by actuating the manipulation prong, in particular from its neutral position (with the transverse axis arranged parallel to the longitudinal axis or running essentially parallel to the same), preferably over a pivot angle β where $0° \leq \beta \leq 80°$ relative to the longitudinal axis of the positioning tool. As a result, the cage can be rotated into the given, predefined relative position in the intervertebral disk compartment in a simple manner, regardless of the selected surgery access route, and can be placed at the prespecified position in the intervertebral disk compartment.

The coupling element of the first manipulator prong and/or the coupling element of the first coupling prong can each be designed according to the invention as a profile projection with a preferably circular cross-sectional shape. Each profile projection extends away from the respective prong in a radial direction. The coupling elements preferably have a circular cylindrical shape. As a result, forces can be transferred to the cage during the implantation which are adequate to enable depositing it against a resistance in its prespecified position in the intervertebral disk compartment. The edges of the coupling elements can be chamfered or rounded. This can counteract undesired tilting or unwanted interlocking of the instrumentation segment with the cage.

To establish a captive mechanical coupling of the coupling prong to the cage, the positioning instrument preferably has a first locking means. This locking means is preferably mounted in a longitudinally displaceable manner in or on the base body of the instrumentation segment and can be displaced in the axial direction relative to the coupling prongs between a releasing position which enables the coupling prongs coupled to the cage to detach and a locking position which locks the coupling prongs coupled to the cage. All in all, this enables the instrumentation segment to be attached to the cage in a manner that is even more stable, and simultaneously detachable.

According to the invention, the insertion opening of the cage can have a clear height which allows the locking means to be supported in its locking position in the direction of the vertical axis of the cage on a wall region of the cage delimiting the insertion opening. As a result, the coupling prong of the positioning instrument can be easily secured in its coupling position on the cage.

The first locking means can preferably be actuated via the actuating segment of the positioning instrument. For example, the actuating segment can therefore have a handle which is mounted so as to be rotatable and/or translationally displaceable and which is movement coupled to the first locking means. This handle can be reversibly connected to the actuating segment or can be inserted into the actuating segment if required.

According to a preferred embodiment of the invention, the instrumentation segment can have a second coupling prong arranged parallel to the first coupling prong. This means that the positioning instrument can be reversibly coupled to the cage even more securely. In this embodiment, the first locking means in its locking position is preferably arranged, in its locking position, with its free end section between the first and the second coupling prongs of the instrumentation segment, in order to prevent the two coupling prongs from nearing each other, and to prevent an associated disconnection of the two coupling prongs from the cage. By moving the locking means into its locking position between the two coupling prongs, these can be spread apart relative to each other if necessary. This embodiment enables a particularly secure and even more reliable coupling of the instrumentation segment to the cage. At the same time, moments in the coupling area can be absorbed even better. A premature disconnection of the cage from the positioning instrument can be ruled out in a particularly reliable manner.

According to the invention, the positioning instrument can have a second locking means which is mounted in a longitudinally displaceable manner in or on the base body of the instrumentation segment, and which can be displaced axially relative to the manipulator prong (as well as relative to the coupling prong) between a releasing position and a locking position arresting the manipulator prongs on the cage. Overall, greater forces can be transmitted to the cage by means of the manipulator.

If the insertion opening of the cage has such a sufficient unobstructed height to enable the second locking means to be supported in its locking position in the direction of the vertical axis of the cage on a wall region of the cage delimiting the insertion opening, the manipulator prongs can be secured in a very simple manner in the position of use thereof when coupled to the cage.

According to the invention, the instrumentation segment can have a second manipulator prong running parallel to the first manipulator prong. In its locking position, the above-described second locking means in this configuration is arranged between the two manipulator prongs, preferably in sections and in particular with its free end section, in order to block the same from nearing each other (and thus to prevent their disconnection from the cage). As a result, both manipulator prongs can be secured with only one locking means when in their functional position coupled to the cage.

The first and the second manipulator prongs are preferably arranged on the instrumentation segment in a manner enabling synchronization of displacement in the direction of the longitudinal axis of the positioning instrument. For this purpose, the two manipulator prongs can, for example, be fastened to each other or formed integrally with each other. If the coupling elements of the two manipulator prongs are each designed in the form of a profile projection, then the coupling elements preferably point away from the respective manipulator prongs in opposite directions.

The aforementioned locking means can preferably be held by a friction fit in its locking position between the one manipulator prong and the cage or between the two manipulator prongs. As a result, the locking means can be moved synchronously together with the manipulator prongs, without being moved out of its locking position.

According to a preferred embodiment of the invention, the individual manipulator prongs and/or the two aforementioned manipulator prongs can be actuated via an actuating segment, i.e. they can be displaced in an axial direction with respect to the longitudinal axis of the positioning instrument.

According to a preferred embodiment of the invention, the first locking means and/or the aforementioned second locking means is/are designed in the form of a rod-shaped locking slide. The locking slide can be made of plastic or metal.

The locking slide is preferably guided in a guide channel of the instrumentation segment.

The manipulator prong(s) is/are preferably arranged, in particular molded on, a manipulator (slide). The manipulator can be designed as a sleeve. The aforementioned second locking slide can be guided within the sleeve.

According to the invention, the first and/or the second locking means can preferably be actuated via the actuating segment. This simplifies handling and allows a low-trauma implantation of the cage.

From the point of view of production technology and also from the point of view of cost, the instrumentation segment and the actuating segment are preferably each designed as instrument modules which can be releasably coupled to each other. Such a modular structure can also increase the range of applications for the cage positioning system. The cage positioning system can thus comprise a plurality of instrumentation segments, each with a cage that is already connected to it and ready for use. These can be provided in the form of a sterile set. The surgeon can then intraoperatively select the sterile set whose cage is most suitable to the individual requirements. The instrumentation segment can then be coupled on and used on the (universally employable) actuating segment.

The instrumentation segment of the positioning instrument is preferably designed for single use according to the invention. In this case, the instrumentation segment can be realized with cheaper materials and does not have to be designed taking into account the requirements of repeated hygienic preparation (cleaning/sterilization). However, it is also conceivable that the instrumentation segment can be dismantled and can be at least partially designed for multiple use. In this case, the instrumentation segment is not completely designed for single use. The hygienic re-preparation of individual parts, in particular the base body and the instrumentation segment, means that a complete new purchase and the associated costs can be avoided.

In contrast to the instrumentation segment, the actuating segment according to the invention is preferably designed for multiple use. For example, it can preferably be sterilized several times and can consist at least partially, preferably completely, of metal, in particular of stainless steel. If the actuating segment can be disassembled into its individual parts, defective parts can be replaced inexpensively if required. This can also further simplify its maintenance and hygienic preparation.

According to a particularly preferred embodiment, the cage has a head segment and a foot segment which can be pivoted relative to each other about a pivot axis. The pivot axis is preferably aligned running parallel to the transverse axis of the cage. As a result, the cage can easily be individually adapted to a desired angular position of the vertebral bodies adjacent to the intervertebral disk compartment intended for receiving the cage. In the neutral position of the cage, the top or upper surface of the head segment and the bottom or base surface of the foot segment are preferably arranged running parallel to each other or essentially parallel to each other.

In the angled or deflected state of the head and foot segments, the top and the bottom together form an angle $\alpha$. The angle $\alpha$ is preferably open to the front of the cage.

If the foot segment and the head segment can be freely pivoted relative to each other in the initial state of the cage, then after the cage has been positioned in the intervertebral disk compartment, a (hyper) lordosis of the spine can be intentionally created in order to set the desired pivot angle or set angle between the head segment and the foot segment.

Due to the required compact constructed size of the cage, the head segment and the foot segment according to the invention are advantageously guided on each other and connected to each other via at least one tongue and groove connection, preferably via two such tongue and groove connections. In the present application, a tongue and groove connection is also understood to mean plowed and tongue connections. With such a tongue and groove connection, on the one hand, a (purely) pivot-joint coupling of the two components can be realized in a very small space. Additional joint components are not necessary. In addition, the two components can easily be captively connected to each other by such a tongue and groove connection. This benefits patient safety.

According to a preferred embodiment of the invention, the cage has a fixing element by means of which the foot segment and the head segment can be fixed in position relative to each other in their respective pivot position, i.e. in their respective set angle. The fixing element can in particular be designed in the form of a screw, for example a so-called grub screw. A screw-in area of the cage is used to hold the fixing screw. The screw-in area (instead of a mating thread) can have simple corrugations or ribs which allow the fixing screw to be positively and frictionally engaged. This enables the fixing screw to be securely seated on the cage regardless of the set angle of the two cage segments. The fixing screw preferably has a driving profile in the form of an internal hexagon or another internal multi-tooth profile.

The cage positioning system preferably comprises a turning tool by means of which the fixing screw can be actuated, preferably by the actuating section. According to the invention, the turning tool can be formed by the first locking means explained above. This enables the number of required components to be kept small. This offers cost advantages.

The actuating segment and the instrumentation segment can preferably be plugged into each other and locked against each other by means of a locking means. The locking means can be designed like a rocker according to the invention.

The actuating segment can have a handle by means of which the manipulator prong(s) can be actuated. In this case, the actuating segment preferably has a display by means of which the given angle of rotation of the cage can be read relative to its neutral position and/or to the longitudinal axis of the positioning instrument.

The coupling prong(s) of the instrumentation segment explained above can in particular be molded onto the base body of the instrumentation segment. As a result, the base body can be designed as a so-called CNC component (computerized numerical control component) or as an injection molded part, or it can be produced by means of a 3D printing process. The base body preferably has a plurality of guide channels in which the manipulator prong(s), the locking means(s) and/or the turning tool are guided.

According to the invention, the cage preferably consists at least partially, preferably completely, of titanium or a titanium alloy or of a cobalt-chromium alloy (Co—Cr alloy). This ensures both a sufficiently high load-bearing capacity and also the required biocompatibility of the cage.

The cage according to the invention is provided for a cage positioning system explained above and comprises an insertion opening for the instrumentation segment of the positioning instrument, as well as coupling means which are each designed to engage with one of the coupling elements of the positioning instrument. The cage preferably has a head segment and a foot segment, which can be pivoted relative to each other about a pivot axis. The pivot axis is preferably arranged parallel to the transverse axis of the cage.

The coupling means of the cage are preferably arranged at a distance from each other on the cage in the direction of the transverse axis of the cage.

The positioning instrument according to the invention is provided for a cage positioning system and preferably has an instrumentation segment designed for single use.

BRIEF DESCRIPTION OF THE DRAWINGS

Further advantages of the invention result from the description and the drawings. The embodiments shown and described are not to be understood as an exhaustive enumeration but rather have exemplary character for the description of the invention.

In the drawings.

DETAILED DESCRIPTION OF THE PREFERRED EMBODIMENTS

Figure 1:
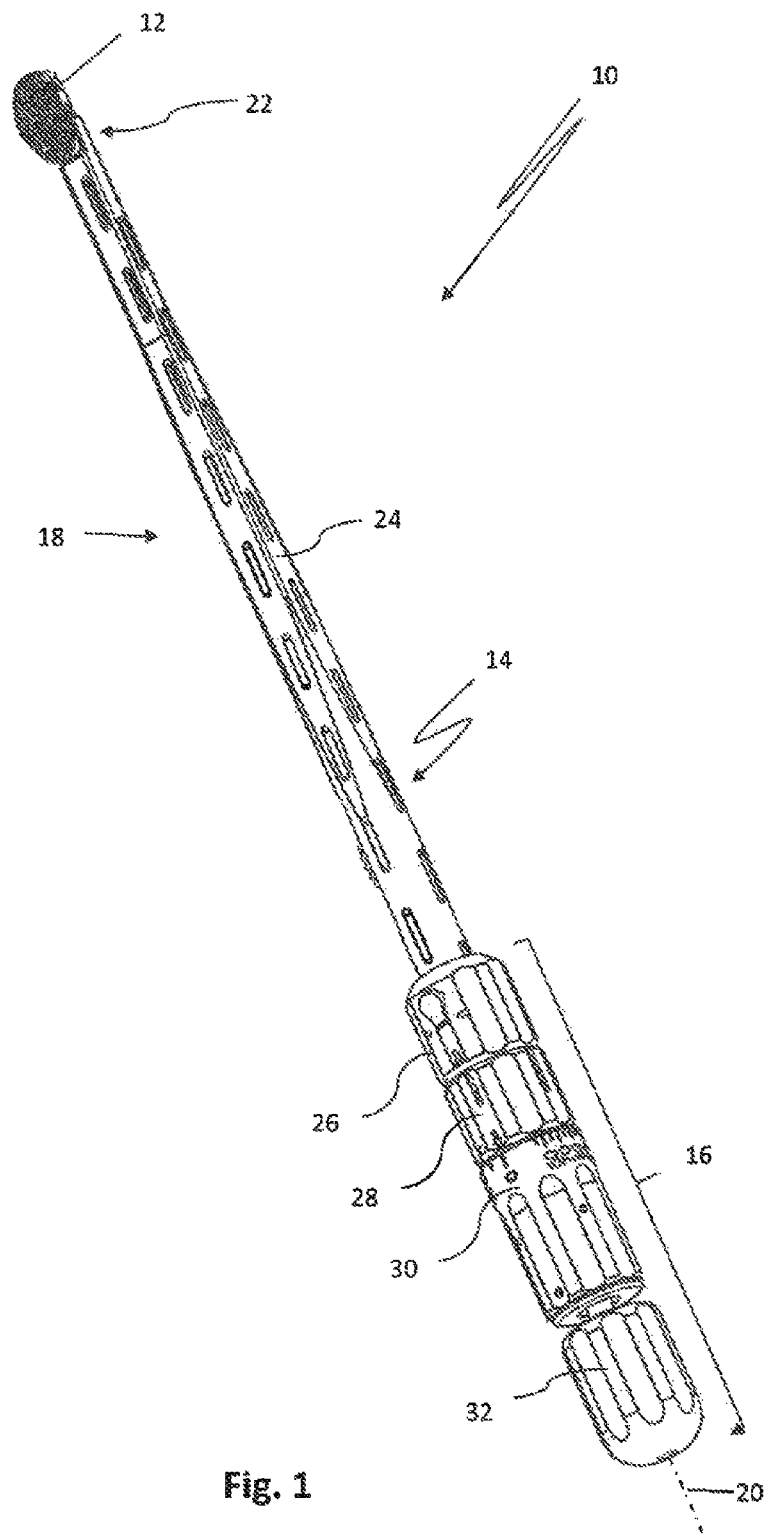
FIG. 1 is a perspective view of a cage positioning system having a positioning instrument with an instrumentation segment and an actuating segment, with a cage coupled to the positioning instrument.

FIG. 1 shows a cage positioning system 10 comprising a cage 12 serving as an intervertebral disk replacement and a positioning instrument 14 for implanting the cage 12 in an intervertebral disk compartment of the spine. The positioning instrument 14 comprises an actuating segment 16 and an instrumentation segment 18 which extends away from the actuating segment 16 in the direction of the longitudinal axis 20 of the positioning instrument 14. The instrument segment 18 is detachably coupled in this case to the cage 12 by its free end 22. The instrumentation segment 18 comprises a base body, designated as 24, which is designed as a hollow body. The base body 24 preferably consists of stainless steel or a plastic.

The actuating segment 16 comprises a plurality of handles 26, 28, 30, 32, the individual functions of which are explained below.

Figure 2:
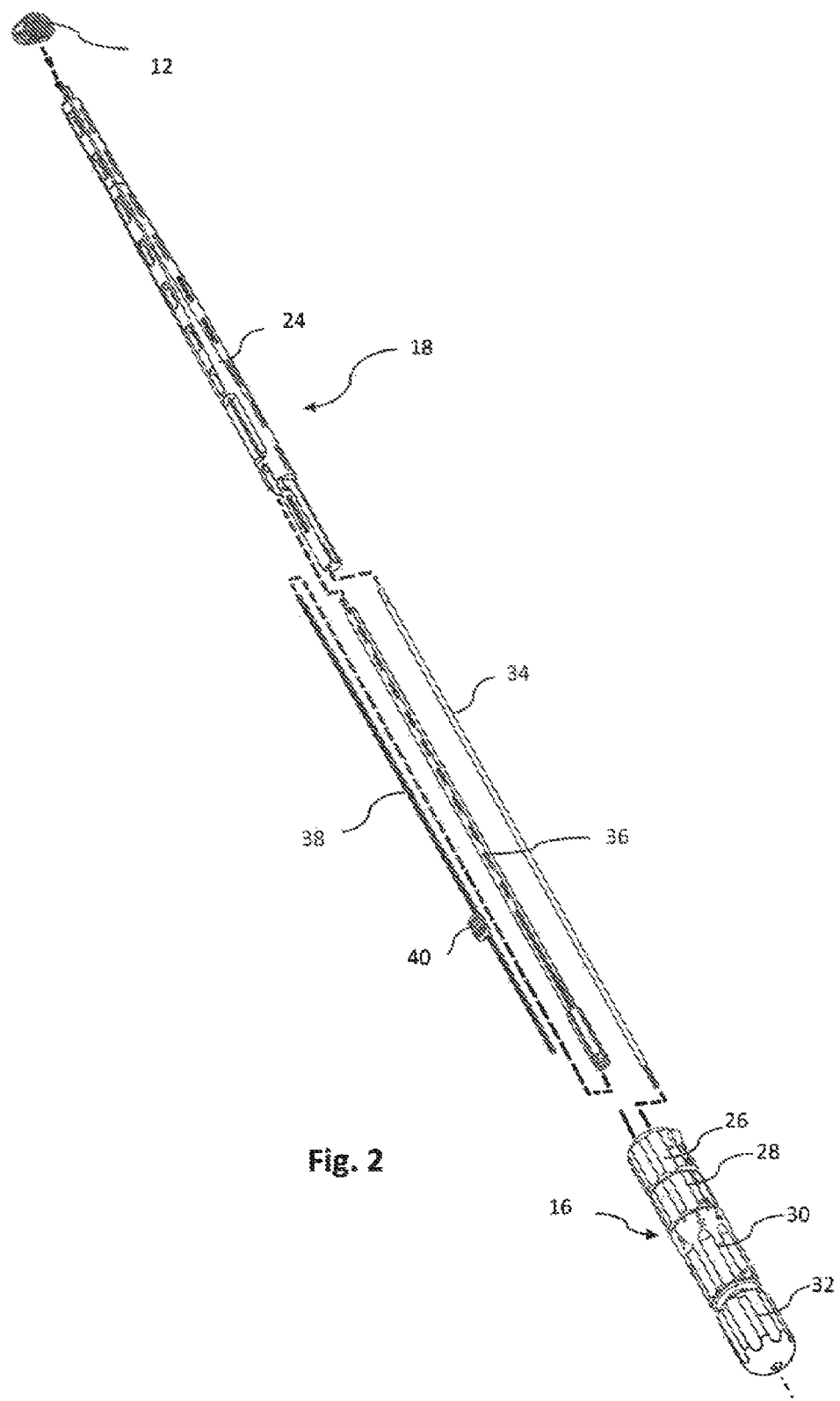
FIG. 2 shows the cage positioning system according to FIG. 1 in a partially exploded view of its parts, in a perspective view.

FIG. 2 shows the cage positioning system 10 in a partially exploded illustration of its parts. The cage 12 is decoupled from the instrumentation segment 18. A first locking means in the form of a first locking slide 34, a manipulator 36, and a second locking means assigned to the manipulator 36, in the form of a second locking slide 38, are guided longitudinally displaceably within the base body 24. The second locking slide 38 is provided with a carriage-like handle 40, which can be provided with a corrugated finger rest. The handle 40 is mounted on the base body 24 so as to be longitudinally displaceable.

The instrumentation segment 18 and the actuating segment 16 are each formed in this case as separately manipulable and preassembled units or instrument modules which can be detachably coupled to each other for the operational use of the positioning instrument 14.

The instrumentation section 18 is preferably designed for single use. In contrast, the actuating segment 16 is preferably designed for multiple use. The actuating segment 16 consists at least partially, preferably entirely, of metal, in particular stainless steel. Alternatively, the actuating segment can consist of a particularly high-quality plastic that is suitable for repeated sterilization measures.

Figure 3:
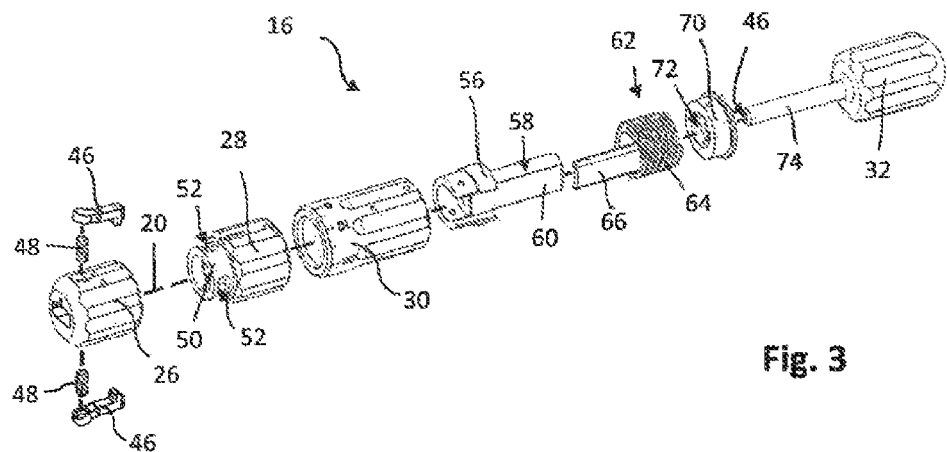
FIG. 3 shows the actuating segment of FIG. 1 in a partially exploded view of its parts, in a perspective view.

In FIG. 3, the actuating segment 16 is shown in a partially exploded view of its individual parts.

The first handle 26 is arranged on the actuating segment 16 at a distal position in the axial direction. This first handle 26 serves as a locking knob for the instrumentation segment 18 to be inserted into the second handle 28. For this purpose, the first handle 26 has an insertion opening 42 on its end face for the instrumentation segment 18. The insertion opening 42 has a cross-sectional shape corresponding to the proximal end section 44 of the instrumentation segment 18. As a result, the instrumentation section can be enclosed in a rotationally fixed manner by the first handle. Locking means 46 are arranged on the first handle 26 and, as shown in FIG. 3, can be designed as rocker-type pawls. In the assembled state, the locking means 46 are held in their respective locking positions in a prestressed manner by spring elements 48 and consequently can be moved into their unlocking position against the force of one of the spring elements 48. According to FIG. 3, the spring elements 48 can each be designed as a compression spring. The first handle 26 is rotatably mounted on a flange 50 of the second handle 28 of the actuating segment 16 serving as a grip section. The flange 50 has engagement recesses 52 for the locking means 46 to axially secure the position of the first handle on the second handle.

Figure 4:
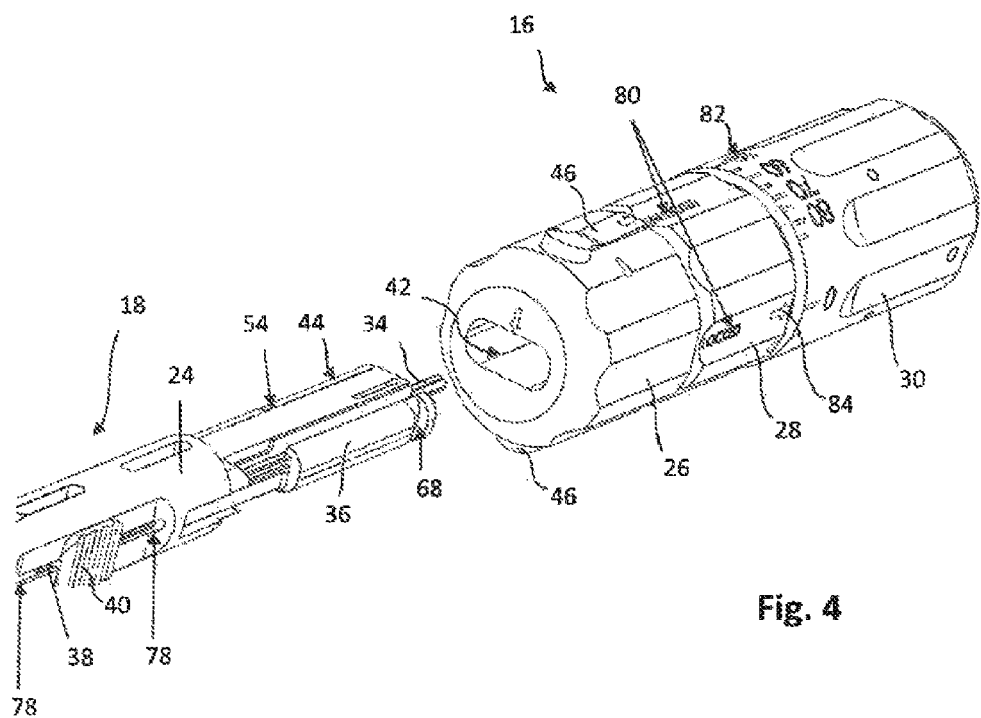
FIG. 4 is a detail of the actuating segment and the instrumentation segment of the positioning instrument according to FIG. 1 before the reversible coupling of the two parts, in a perspective view.

According to FIG. 4, the proximal end section 44 of the instrumentation segment 16 has a groove 54. The inside of the second handle 28 has a locking web which is complementary to the groove 54 and which cannot be seen in FIG. 3 for reasons of illustration. The locking web can be moved relative to the second handle 28 into the groove 54 by rotating the first handle 26 with the instrumentation segment 18 inserted via the insertion opening 42 into the first and second handles 26, 28 up to the stop. As a result, the instrumentation segment 18 can be fixed in position on the second handle 28 in the axial direction (reversibly). An unintentional detachment of the instrumentation section 18 from the actuating section 16 is ensured by the locking means 46 engaging in the engagement recesses 52.

A third handle 30 adjoins the second handle 28 in the axial direction. The third handle 30 can be rotated about the longitudinal axis 20 relative to the second handle 28 in the assembled state of the actuating segment 16. A bearing sleeve 56 with a bearing pin 58 is arranged within the second and third handles 28, 30 and extends here proximally away from the bearing sleeve 56 in the axial direction. The bearing sleeve 56 is pinned to the second handle 28. The bearing pin 58 has a flattened peripheral region 60. Reference number 62 indicates a movement sleeve which, in the assembled state of the actuating segment 16, has a threaded connection via its external thread 64 to the third handle 30. The movement sleeve 62 has a partially circumferentially flattened plunger 66 which, in the assembled state of the positioning instrument, abuts in sections the bearing pin 58 of the bearing sleeve 56 and is guided in a longitudinally displaceable manner.

A driver which projects inwards away from the movement sleeve 62 in the radial direction is arranged on the inside of the plunger 66 of the movement sleeve 62. When the instrumentation segment 18 is coupled to the actuating segment 16, the driver engages in a holding groove 68 of the manipulator 36 in order to couple its movement in the axial direction with the movement sleeve 62. The movement sleeve 62 is held within the third handle 30 by means of a cover ring 70. The cover ring 70 can be pinned to the third handle 30. The cover ring 70 has an axial passage 72 through which a fourth handle 32 designed as a rotary knob can be inserted into the second handle 28 of the actuating segment 16, by a driver pin 74. The driver pin 74 has at its distal end a driver profile 76—in this case, an inner polygonal profile. The inner polygonal profile serves to accommodate the first locking slide, designated as 34 in FIGS. 2 and 4, which extends into the actuating segment 16 at one end, in the assembled state of the positioning instrument 14.

In FIG. 4, the fifth handle 40 of the positioning instrument, which is arranged on the instrumentation section, can be clearly seen. The fifth handle can be moved back and forth in the axial direction between two end positions 78. The function of the fifth handle 40 is explained further below.

The second handle 28 has first markings 80 via which the locked state of the first handle 26, along with the instrumentation segment 18, can be read relative to the second handle 28—in this case, the locking means 46 thereof. The third handle 30 has second markings 82 with angle information that can be read relative to a reference mark 84 of the second handle.

Figure 5:
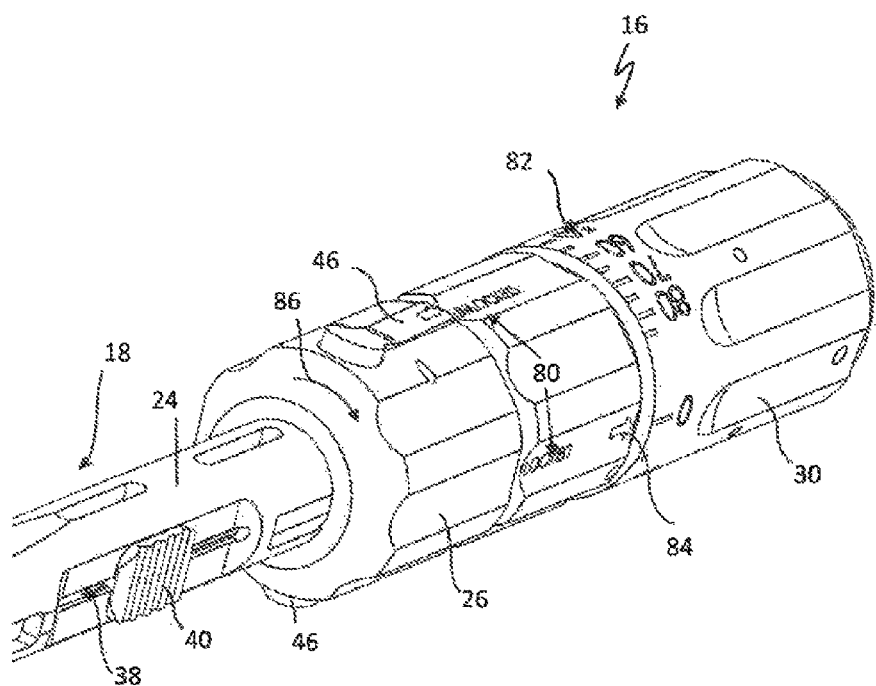
FIG. 5 is a detail of the actuating segment and the instrumentation segment of the positioning instrument according to FIG. 1, in a perspective view.

FIG. 5 shows the instrumentation segment 18 in its prespecified installation position inserted into the actuating segment 16. The instrumentation segment 18 can be locked in the actuating segment 16, i.e. fixed in position in the axial direction, by rotating the first handle 26 in the direction of arrow 86.

Figure 6:
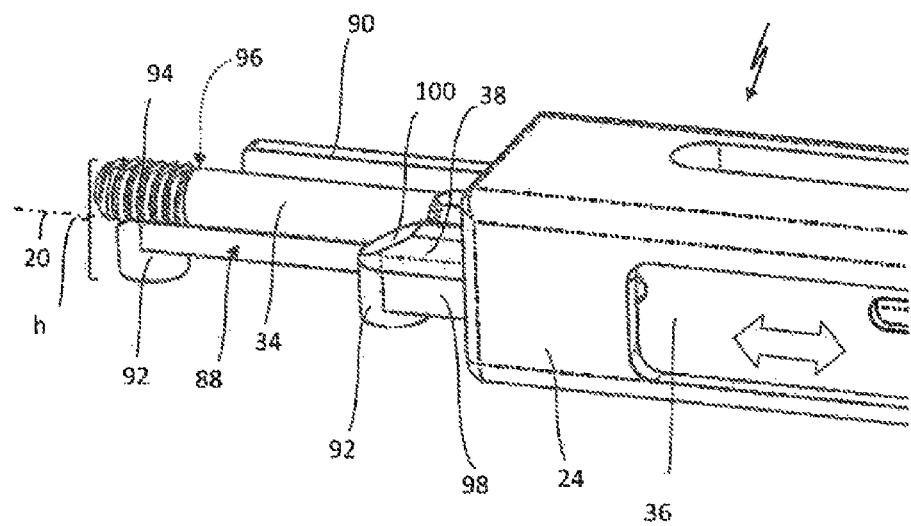
FIG. 6 is a detail of the instrumentation segment of the positioning instrument according to FIG. 1, in a perspective view.

An enlarged detail of the distal end of the instrumentation segment 18 is shown in FIG. 6. The base body 24 of the instrumentation segment 18 has a coupling prong 88 at one end, which extends away from the base body 24 in the axial direction. The coupling prong 88 can have an angled edge region 90 in order to ensure sufficient stiffness of the coupling prong 88. In this case, the coupling prong 88 has an L-shaped or essentially L-shaped cross-sectional shape.

A coupling element 92 is arranged on the free end section of the coupling prong 88. The coupling element 92 extends laterally away from the coupling prong 88 in the radial direction. In the present case, the coupling element 92 is designed in the shape of a circular cylinder. The first locking slide 34 (upper side) explained in connection with FIG. 5 lies against the coupling prong 88. The first locking slide 34 is laterally splinted through the angled edge region 90 of the coupling prong 88.

A fixing element 94, here in the form of a grub screw, for example, can be arranged at the free end of the first locking slide 34. The fixing element 94 can have a driving profile (not shown in more detail), for example in the form of a hexagon socket, in which the locking slide 34 engages in a rotationally fixed manner (with an external hexagon or so-called Allen key). Alternatively, the fixing element 94 can also be integrally connected to the locking slide 34. In this case, the locking slide 34 and the fixing element 94 are advantageously connected to each other via a predetermined breaking point 96 in order to be able to separate the locking slide 34 from the fixing element 94 after the fixing element 94 has been placed. It is also conceivable that the fixing element 94 is glued to the first locking slide 34 or arranged on the locking slide 34 in a press fit. The locking slide 34 can alternatively have a tool profile, for example an Allen key, which detachably engages in a corresponding driving profile (=drive profile) of the fixing element 94. The fixing element 94 is preferably designed as a screw.

The manipulator 36 has a manipulator prong at one end, designated by 98. The manipulator prong 98 has, in a manner corresponding to the coupling prong 88, a coupling element 92 which extends from the manipulator prong 98 in the radial direction—i.e. extends away from the same. The coupling elements 92 of the two prongs can extend in the same direction from the given prong as shown in FIG. 6 or, according to an embodiment not shown in the drawing, in opposite directions from the respective prong.

A second locking slide 38 is assigned to the manipulator 36. The second locking slide 38 can lie directly against the manipulator prong 98 and can be supported thereon in a radial direction. The free end of the locking slide 38 can have an insertion chamfer 100. The cumulative height h of the coupling prong 88 and the first locking slide 34 assigned to the coupling prong 88, as well as the cumulative height h of the manipulator prong 98 and the assigned second locking slide 38, can be clearly seen in FIG. 6.

Figure 7:
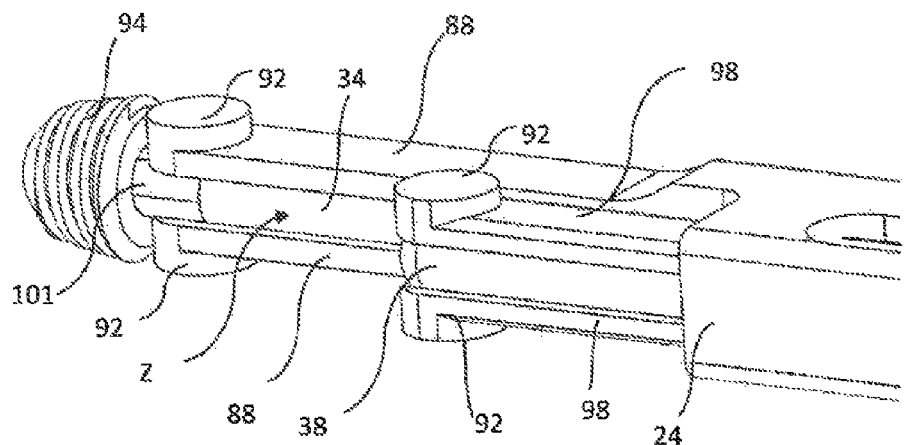
FIG. 7 shows an alternative embodiment of the instrumentation segment of the positioning instrument according to FIG. 1, in a perspective view.

The positioning instrument 14 can have a second coupling prong 88 and/or a second manipulator prong 98 according to the embodiment shown in detail in FIG. 7. The second coupling prong 88 is arranged parallel or substantially parallel to the first coupling prong 88. As a result, an intermediate space Z is formed between the two coupling prongs 88, into which the first locking slide 34 can be advanced in the direction of the longitudinal axis 20 of the positioning instrument 14. The coupling elements 92 of the two coupling prongs 88 point away from the respective coupling prongs 88 in opposite directions. If the first locking slide 34 is pushed forward between the two coupling prongs 88 in the axial direction, this blocks the two coupling prongs 88 from nearing each other. The first locking slide 34 can optionally spread the coupling prongs 88 apart (slightly). According to FIG. 7, the locking slide 34 reversibly engages with a tool profile 101, in this case a so-called Allen key, in a corresponding driving profile of the fixing element 94. The two coupling prongs 88 are preferably integrally formed on the base body 24 and flexibly articulated thereon.

The second manipulator prong 98 is arranged parallel or substantially parallel to the first manipulator prong 98. As a result, an intermediate space Z is formed between the two manipulator prongs 98, into which the second locking slide 38 can be advanced. The coupling elements 92 of the two manipulator prongs 98 point away in opposite directions from the respective manipulator prongs 98. If the locking slide 38 is pushed forward between the two manipulator prongs 98 in the axial direction, this blocks the two manipulator prongs 98 (coupled to the cage) from nearing each other. The second locking slide 38 can, if necessary, spread the manipulator prongs 98 apart (slightly), so that they diverge towards the free end.

Figure 8:
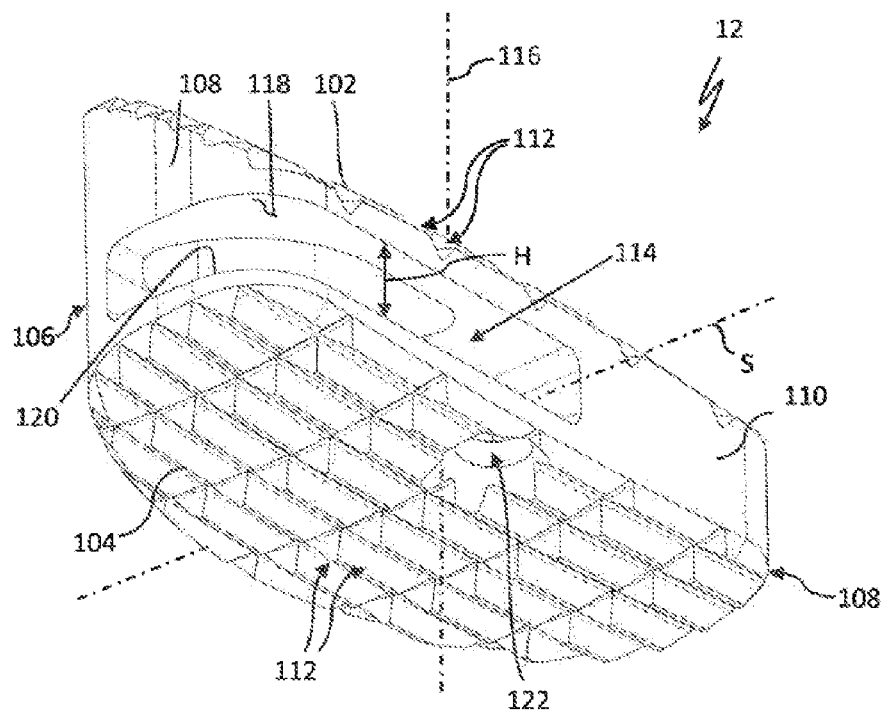
FIG. 8 shows a first embodiment of the cage according to FIG. 1, in a perspective view.
Figure 9:
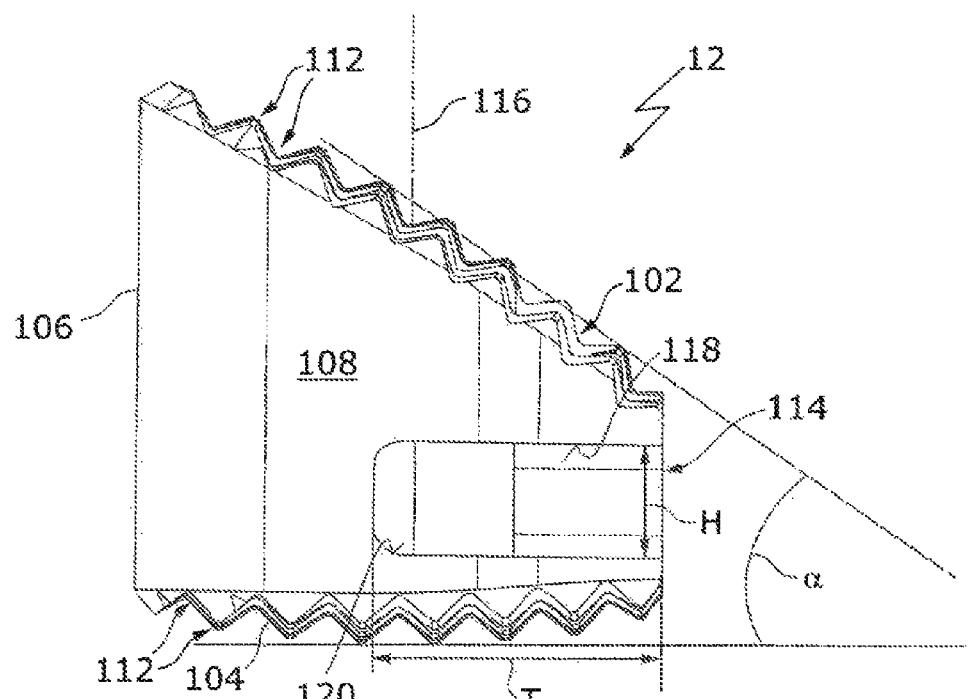
FIG. 9 shows the cage of FIG. 8 in a side view.
Figure 10:
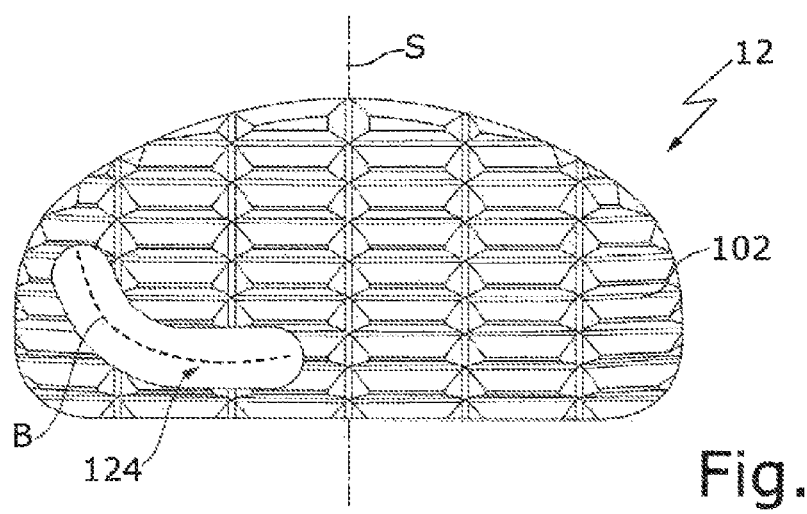
FIG. 10 shows the cage of FIG. 8 in a view of its base.

In FIGS. 8 to 10, a first embodiment of the cage 12 according to FIG. 1 is shown. The cage 12 here has a kidney-shaped basic shape. A top surface (top) of the cage is designated by 102, and its base surface (bottom) arranged opposite is designated by 104. The lateral surface 106 which points forward in the implanted state of the cage 12 in the direction of its sagittal axis S is connected to the rear lateral surface 110 via two opposite lateral surfaces 108. The top surface 102 and the base surface 104 of the cage 12 have a macroscopic surface structure 112, by means of which an improved bony frictional connection and an improved osseointegration of the cage 12 implanted in the intervertebral disk compartment should be made possible.

The cage 12 has an insertion opening, designated by 114, for the instrumentation segment 18 of the positioning instrument 14. The insertion opening 114 extends in the circumferential direction from one of its lateral surfaces 108 to the rear lateral surface 110. A clear height of the insertion opening 114 is denoted by H. The insertion opening 114 is delimited in the direction of the vertical axis 116 of the cage on the upper side by a top wall 118 and on the underside by a bottom wall 120.

The bottom wall 120 is provided with a first coupling means 122. The coupling means 122 in this case is in the form of a recess for the engagement of the coupling element 92 of the coupling prong 88 of the positioning instrument 14. The top wall 118 of the insertion opening 114 is provided with a second coupling means 124 in the form of a non-linear recess, which serves for the engagement of the coupling element 92 of the manipulator prong 98.

According to FIG. 9, the top surface 102 and the base surface 104 of the cage 12 are arranged running diagonally at a fixed angle α to each other. As a result, the cage 12 has a triangular cross-sectional shape. The insertion opening 114 has a depth t which corresponds approximately to half the sagittal extension of the cage 112.

It is understood that the orientation of the coupling elements 92 of the coupling prong 88 and the manipulator prong 98 and the arrangement of the corresponding coupling means 122, 124 of the cage 12 are adapted to each other.

Thus, the coupling means 122 for the one coupling element 92 of the manipulator prong 88 can also be arranged or formed on the bottom wall 120 of the insertion opening 114. In a corresponding manner, the coupling means 124 for the one coupling element 92 of the coupling prong 88 can be formed on the top wall 118 of the insertion opening. The second coupling means 124 forms a non-linear movement path B (FIG. 10) for the coupling element of the manipulator prong 98, along which the coupling element 92 can be guided.

Figure 11:
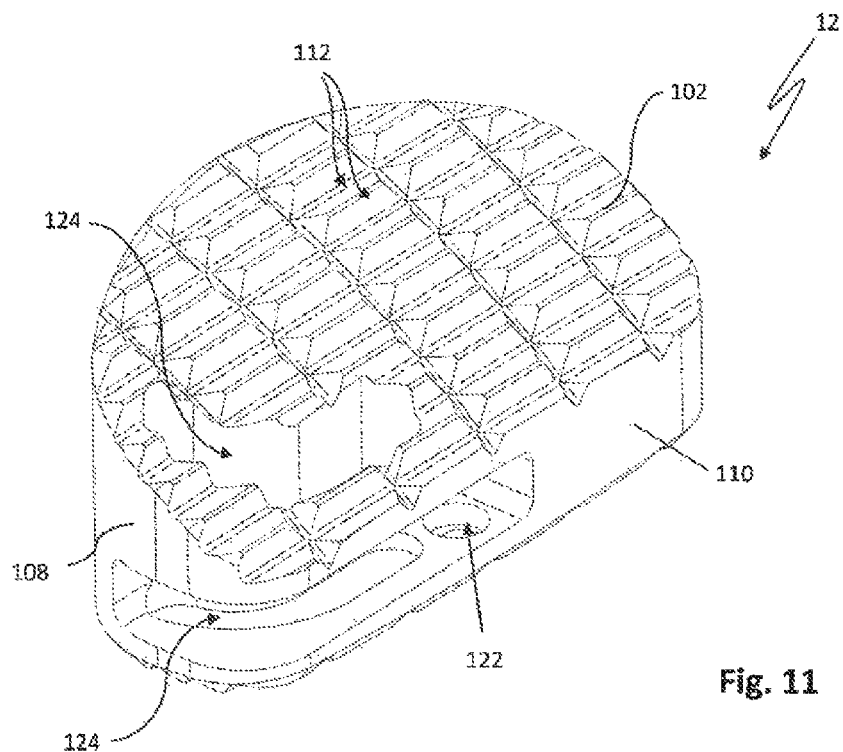
FIG. 11 shows an alternative embodiment of the cage of FIG. 1 in a perspective view.

If the positioning instrument 14 (FIG. 1) has two manipulator prongs 98, the cage 12 accordingly has two second coupling means 124 for the manipulator prongs 98, one of which is are arranged on/in the top wall 118 and the other on/in the bottom wall 120 of the insert opening 114, as shown by way of example in FIG. 11.

Figure 12:
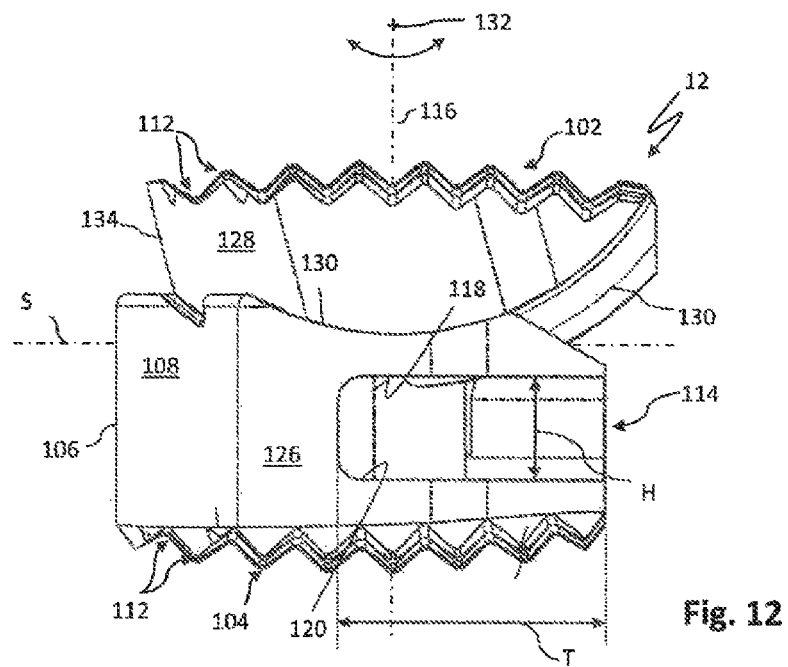
FIG. 12 is a side view of a cage which can pivot in itself, having a foot segment and a head segment which are arranged relative to each other in the neutral position.
Figure 13:
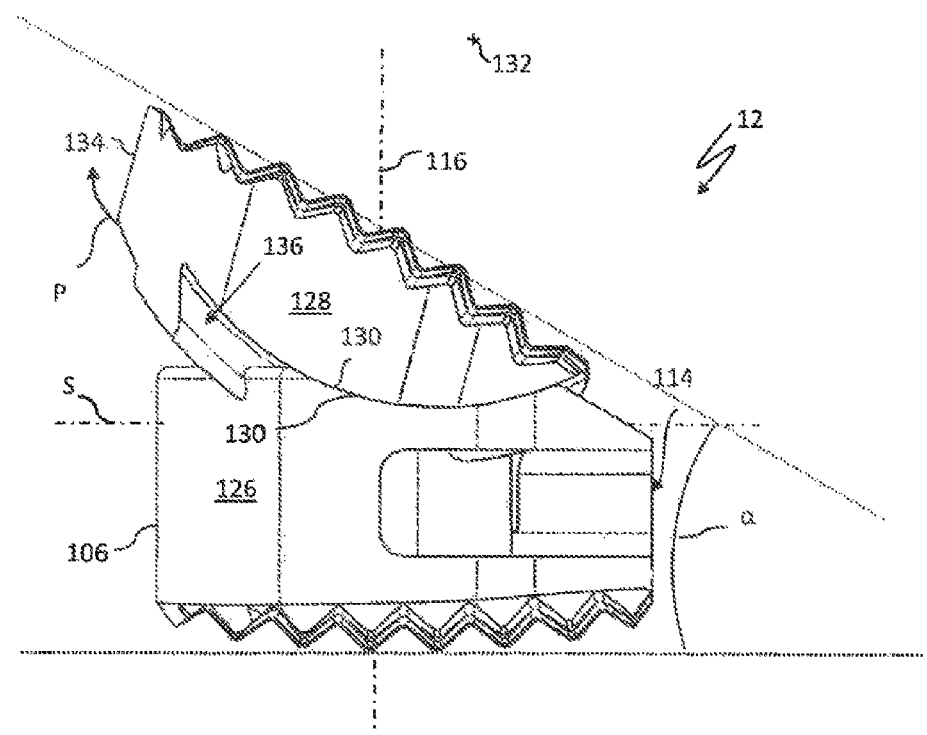
FIG. 13 shows the cage in FIG. 12 in the deflected state of the head segment, in a side view.

FIGS. 12 to 13 show a further exemplary embodiment of the cage 12 of a cage positioning system 10 according to FIG. 1. This cage 12 has a foot segment 126 and a head segment 128, which are connected to each other in an articulated manner. As a result, different lordosis angles of the spine can be assumed by the cage. In FIG. 12, the cage 12 is shown in its neutral position. In the neutral position, the top surface 102 and the base surface 104 are arranged essentially parallel to each other, although the top surface 102 of the head segment 128 and the base surface 104 of the foot segment 126 are each slightly curved outwards.

The foot segment 126 and the head segment 128 have mutually facing joint surfaces 130, by means of which the foot segment 126 and the head segment 128 abut each other. The joint surfaces 130 are each arched in the sagittal direction of the cage 12. The two segments 126, 128 can be pivoted relative to each other about a pivot axis designated by 132. The curvature of the two joint surfaces 130 is such that the pivot axis 132 is arranged far outside of the cage. With an increasing set angle α between the head segment 128 and the foot segment 126, the anterior edge 134 of the head segment is moved in the direction of the sagittal axis S of the cage 12 beyond the front lateral surface 106 of the cage 12, as is illustrated by the arrow P in FIG. 13. As a result, the cage 12 cannot only be variably adapted to different angular positions of adjacent vertebral bodies, but also an improved support of the vertebral bodies is made possible for the lordosis of the lumbar spine.

The head segment 126 and the foot segment 124 of the cage 12 are preferably guided on each other via at least one tongue and groove connection 136, here purely by way of example via two tongue and groove connections 136, and held captively against each other. This eliminates the need for separate joint components.

Figure 14:
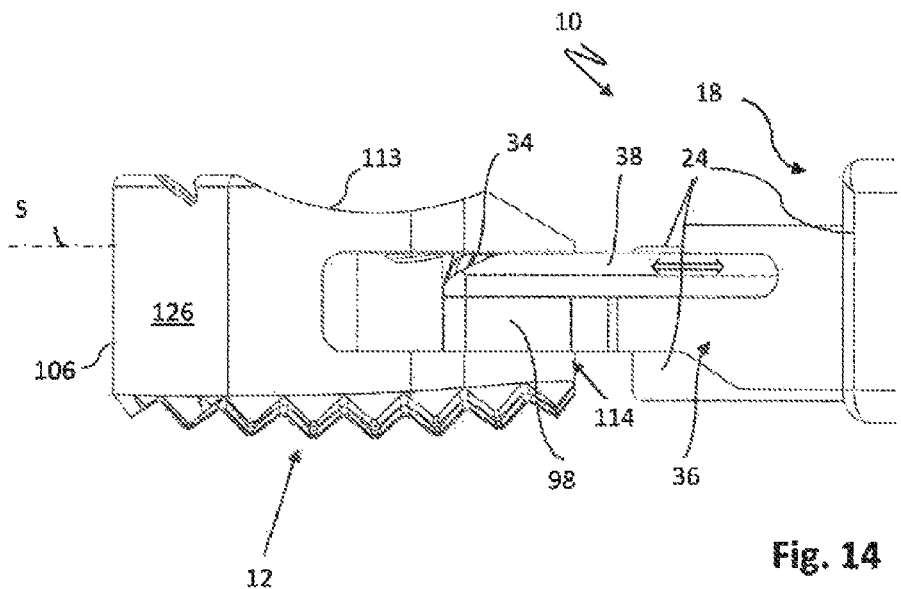
FIG. 14 shows the foot segment of the cage according to FIG. 12 with a positioning instrument coupled thereto, in a side view.

In FIG. 14, the foot segment 126 of the cage 12 according to FIGS. 12 and 13 is shown in a cutaway view with a positioning instrument 14 coupled to it. The positioning instrument 14 has an instrumentation segment according to FIG. 6. The instrumentation segment 18 has only one coupling prong (not shown in FIG. 14 due to the illustration) and only one manipulator prong 98.

Figure 15:
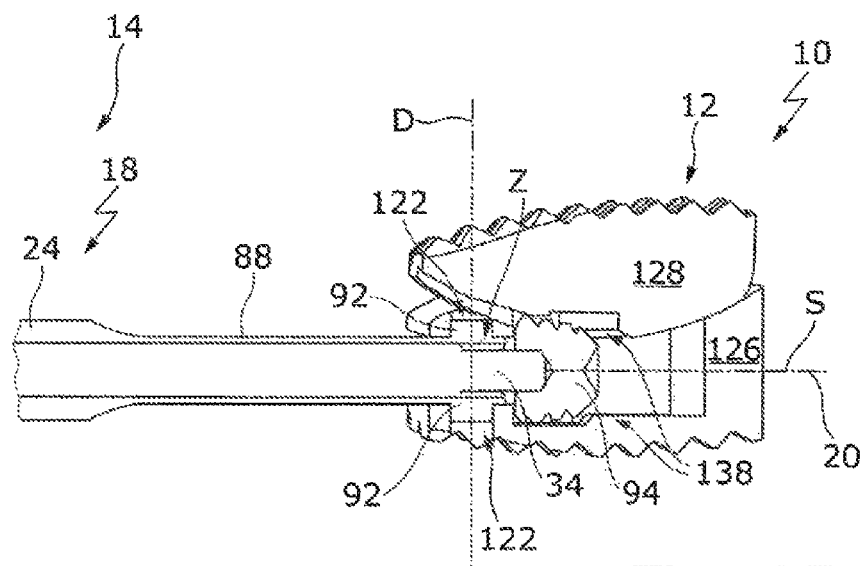
FIG. 15 shows a cage which is similar to the cage according to FIG. 12, with a positioning instrument coupled thereto which has two coupling prongs, each of which is provided with a coupling element, the coupling elements engaging in the corresponding recesses of the cage.

FIG. 15 shows a cage according to FIG. 12 with a coupled positioning instrument 14. The positioning instrument here has two coupling prongs 88 which engage with their respective coupling element 92 in a form-fitting manner in a first coupling means 122 of the cage 12 designed as a bore. The first locking slide 34 assigned to the two coupling prongs 88 is arranged in its (distal) locking position. The two coupling prongs 88 are thereby locked in their coupling position engaging in the locking means.

The fixing element 94 is still fixed on the first locking slide and can be screwed into the screw-in area 138 of the foot segment 126 and the head segment 128 in order to fix them relative to each other after setting a desired set angle α (FIG. 13).

Figure 16:
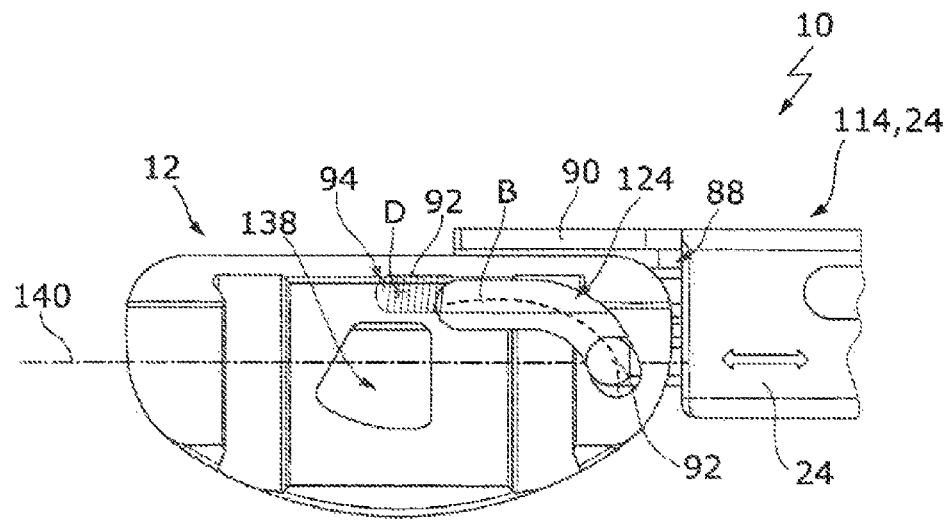
FIG. 16 shows a cage positioning system, the cage of which is arranged relative to the positioning instrument in the neutral position, in a plan view with a partially transparent illustration of the cage.

Functional Description:

FIG. 16 shows a partially transparent top view of the positioning system 10 with a cage 12 and a positioning instrument 14 coupled to it. Reference number 140 indicates the transverse axis of the cage, which is oriented orthogonally to the vertical axis 116 and to the sagittal axis S. The transverse axis 140 of the cage is arranged in its neutral pivot position about the axis of rotation D relative to the longitudinal axis 22 of the positioning instrument and/or the coupling prong(s) 88 of the positioning instrument 14. The non-linear movement path B for the coupling element of the manipulator prong can be seen clearly.

Figure 17:
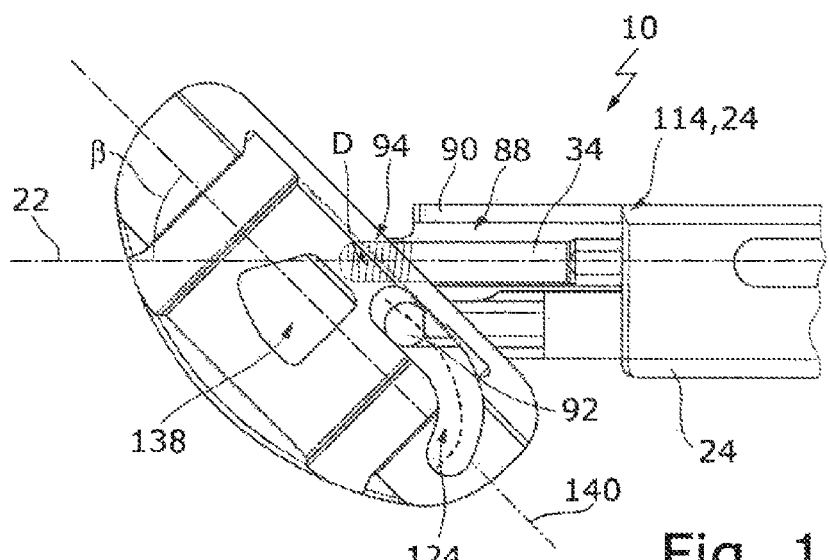
FIG. 17 shows the positioning system of FIG. 16 with the cage pivoted relative to the positioning instrument, in a top view with a partially transparent illustration of the cage.
Figure 18:
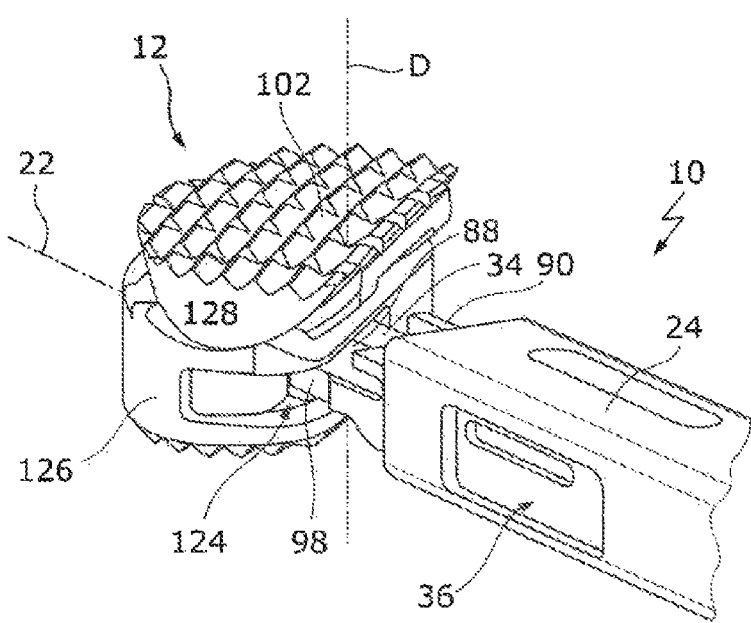
FIG. 18 shows the positioning system of FIG. 17 in a perspective view.

In FIGS. 17 and 18, the cage 12 is arranged with its transverse axis 140 pivoted by a pivot angle β of approximately 45° relative to the longitudinal axis 22 of the positioning instrument 14. In comparison to the neutral position of the cage 12 (FIG. 16), the manipulator 36, together with its manipulator prongs 98, is arranged distally in the axial direction.

Figure 19:
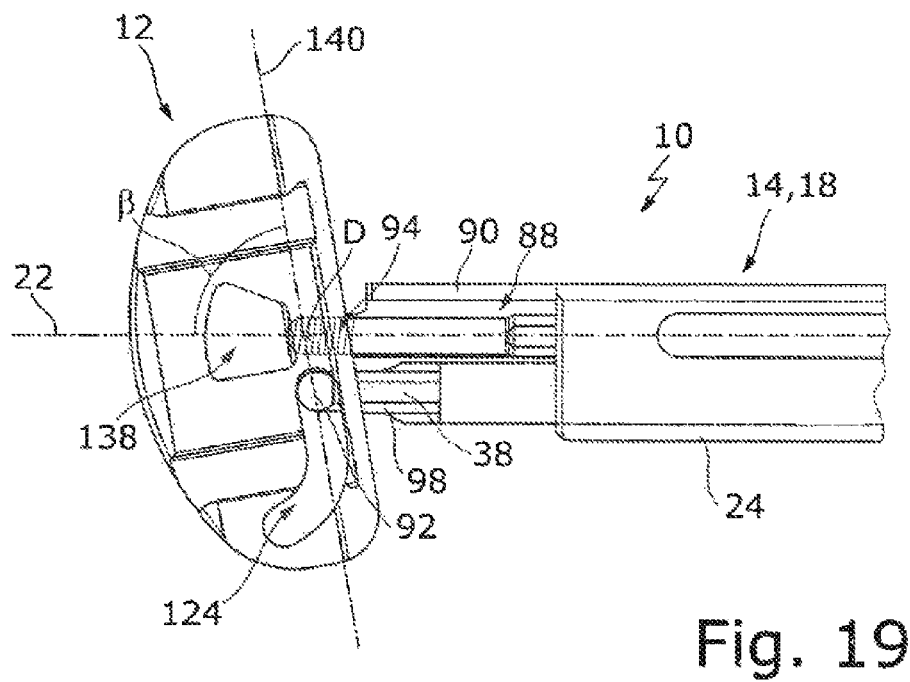
FIG. 19 shows the positioning system of FIG. 16 with a more pivoted cage, in a top view with a partially transparent illustration of the cage.

According to FIG. 19, the cage 12 with its transverse axis 140 forms an angle β of approximately 80° with the longitudinal axis 22 of the positioning instrument and/or the coupling prong. The circular-cylindrical coupling element 92 of the manipulator prong 98 lies against the cage in the end region of the second coupling means 124 of the cage 12, which is designed as a non-linear elongated hole. This prevents further pivoting of the cage 12 about the axis of rotation D.

Figure 20:
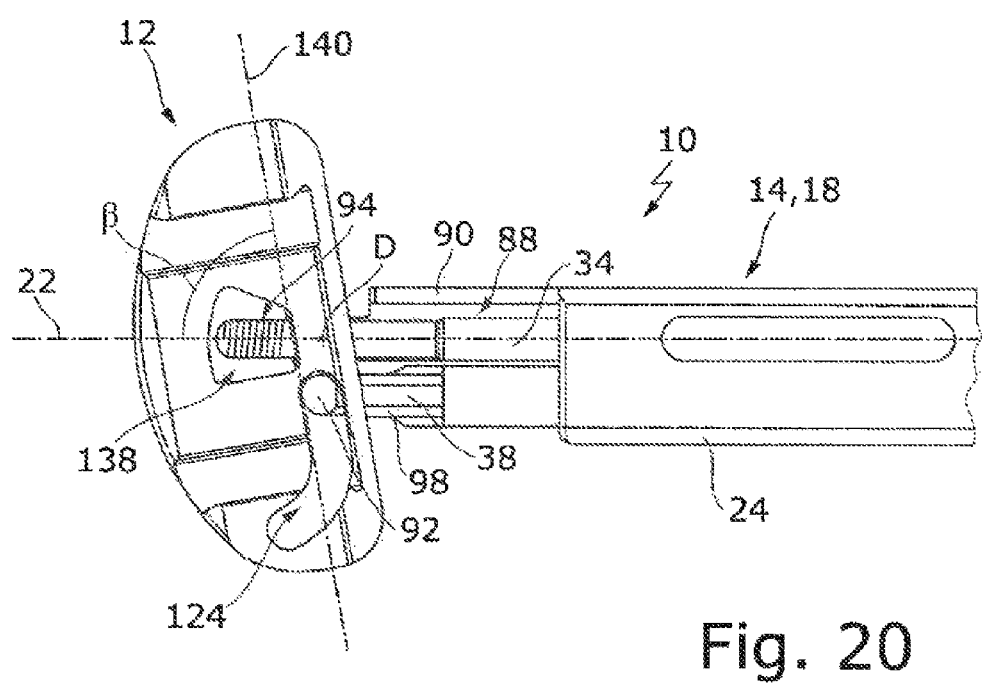
FIG. 20 shows the positioning system of FIG. 19 with the foot and head segment of the cage fixed in position relative to each other, in a top view with a partially transparent illustration of the cage.

In FIG. 20, the fixing element 94 designed as a grub screw is screwed into the screw-in area 138 of the cage 12. The foot segment 126 and the head segment 128 are thereby locked relative to each other in terms of their set angle α.

Figure 21:
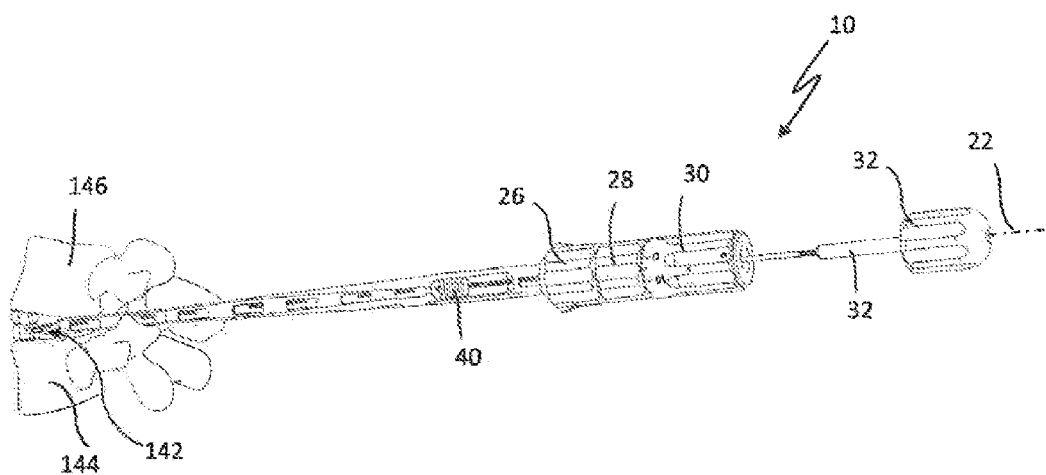
FIG. 21 shows the positioning system of FIG. 1 after the implantation of the cage, in a perspective view.
Figure 22:
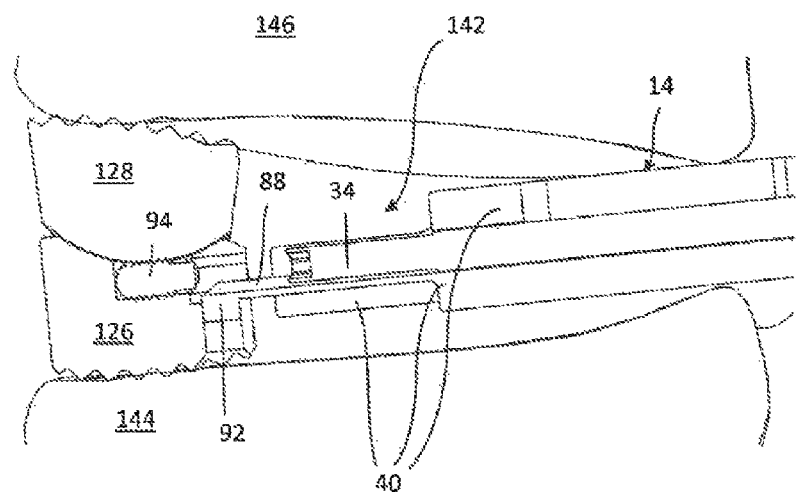
FIG. 22 shows the cage positioning system of FIG. 1 after the implantation of the cage, in side view.

In FIG. 21, the cage 12 is positioned in the intervertebral disk compartment 142 between two physiologically directly adjacent vertebrae of the five human lumbar vertebrae. The fixing element 94 was moved into its fixing position by means of the fourth handle 32 of the actuating segment 16 of the positioning instrument, i.e. screwed into the screw-in area 138 of the cage 10 in this case. The fourth handle 32 can then be moved out of the remaining actuating segment 16 in the axial direction. As a result, the coupling prong 88 is no longer secured in its coupling position on the cage 12 by the first locking slide 34. At the same time, the locking slide 34 serving as a turning tool is disconnected from the fixing element 94, as is shown in more detail in FIG. 22.

Figure 23:
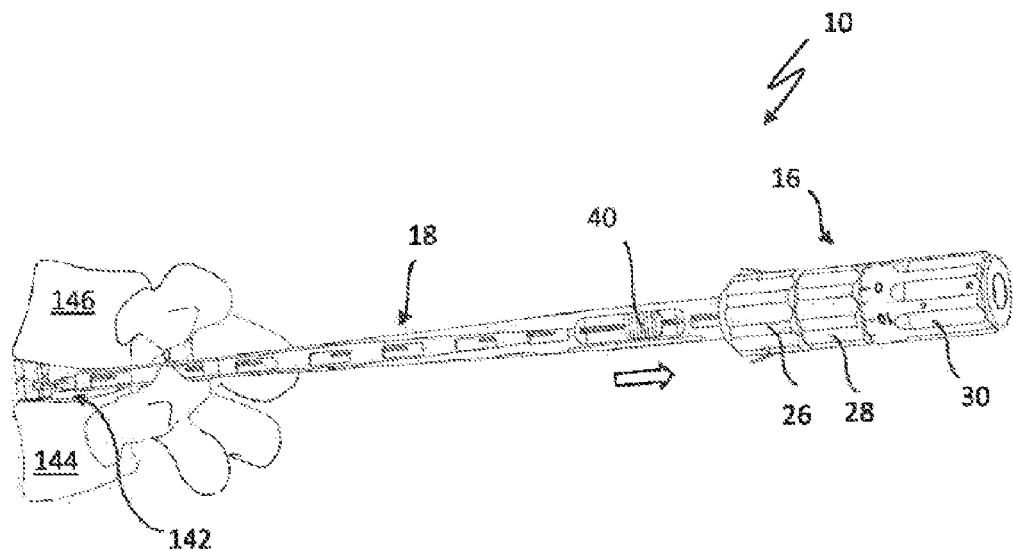
FIG. 23 shows the cage positioning system of FIG. 1 during the unlocking of the instrumentation section, in a perspective view.
Figure 24:
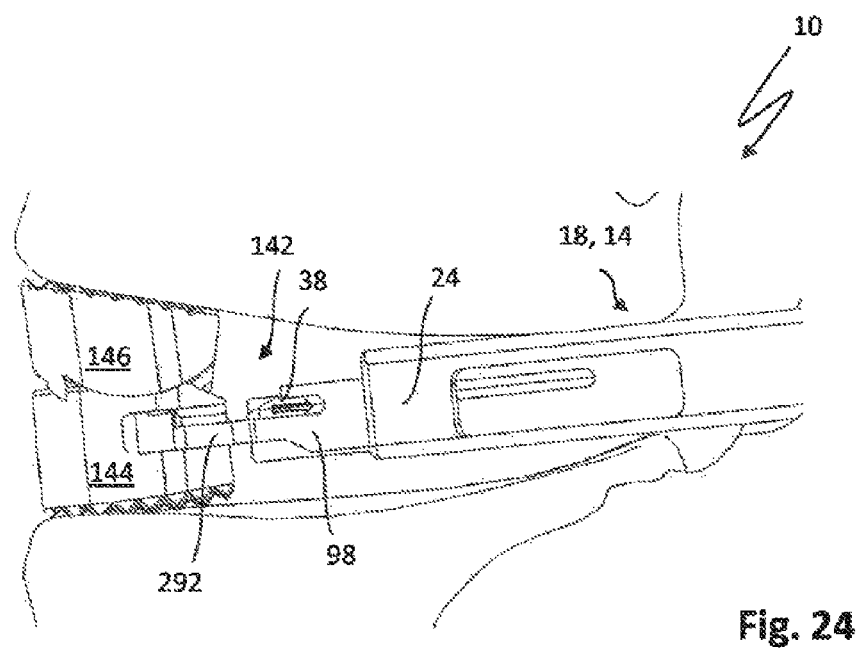
FIG. 24 shows the cage positioning system according to FIG. 23, in a side view.

In FIG. 23, the handle 40 of the instrumentation segment 18 is displaced proximally in the axial direction. As a result, the second locking slide 38 of the manipulator prong 98, which is motion coupled with the handle 40, is transferred to its releasing position which releases the manipulator prong 98 from the cage, as shown in FIG. 24.

Figure 25:
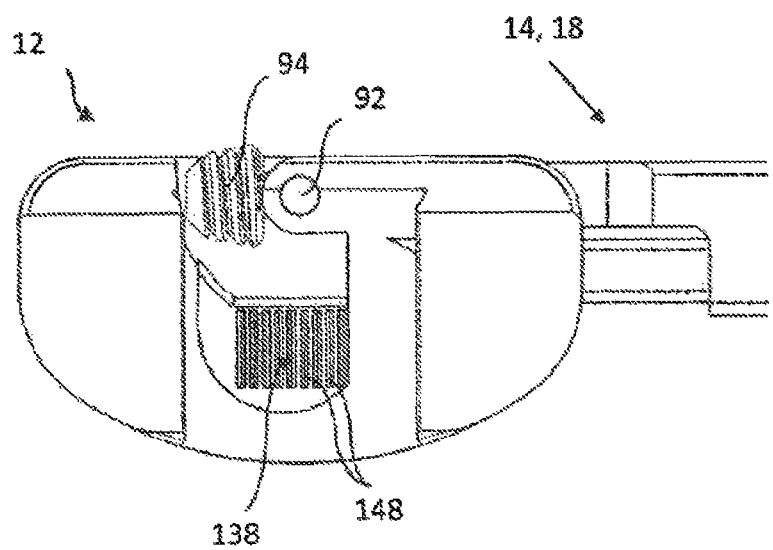
FIG. 25 shows an embodiment of the cage of FIG. 1, in a partially sectioned view.

FIG. 25 shows an articulated cage 12 coupled to the positioning instrument 14. The screw-in area 138 of the cage 12 can have corrugations 148, which are arranged here on the top wall 118 and the bottom wall 120 of the insertion opening 114. The corrugations 148 can also be at least partially a shape which is different from the linear shape shown in FIG. 25.

Figure 26:
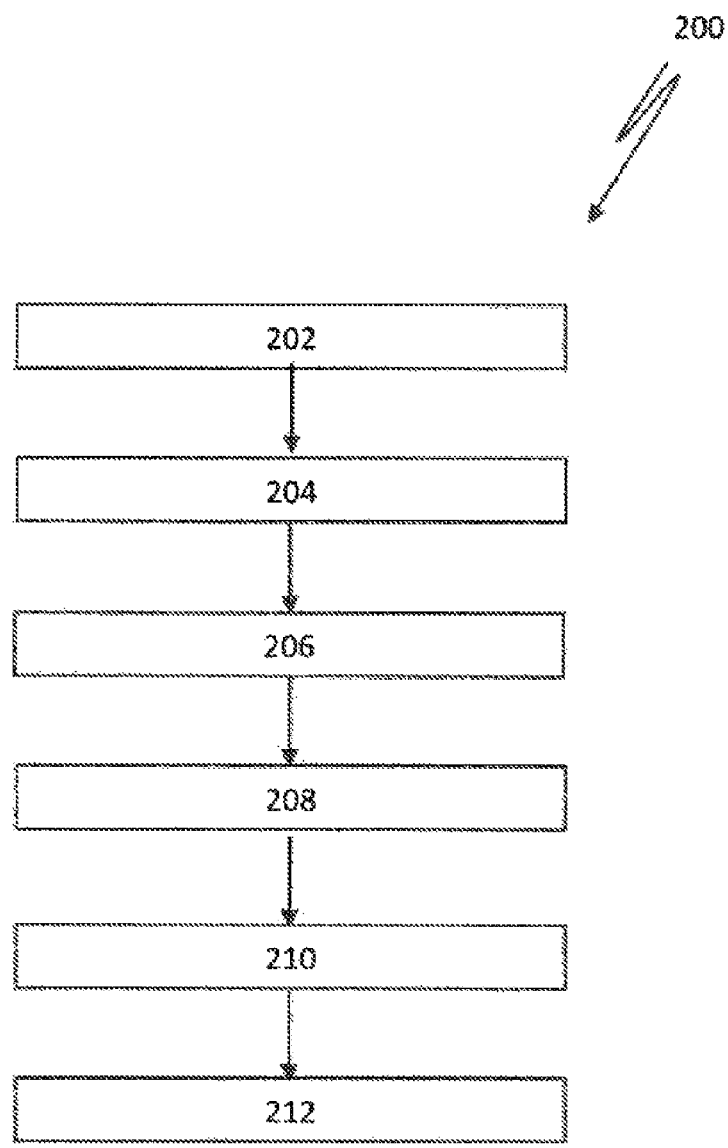
FIG. 26 shows a block diagram with individual process steps for implanting a cage.

The mode of operation of the cage positioning system 10 is explained below with additional reference to the steps of the method 200 for implanting the cage 12 shown in FIG. 26.

In order to implant the cage 12 in the intervertebral disk compartment 142 of the preferably lumbar spine, arranged between two vertebral bodies 144, 146, the positioning instrument 14 is coupled in a first step 202 to the cage 12 with its coupling prongs 88 and its manipulator prongs 98 of the instrumentation section 18.

In a further step 204, the instrumentation section 18 coupled to the cage is secured by moving the first locking slide 34 into its locking position in its position coupled to the cage 12. The instrumentation segment 18 can be provided with the cage 12 pre-assembled in the form of a sterile set.

In a further step 206, the actuating segment 16 is coupled to the instrumentation segment 18 by an operator. For this purpose, the instrumentation segment 18 is inserted into the insertion opening (cf. Fig.) of the actuating section 16 up to the stop in sub-step 206a. The locking means 46 (=pawls) are unlocked in sub-step 206b and the manipulator 36 of the instrumentation segment 18 is brought into engagement with the third handle 30 by its rotational movement about the longitudinal axis 22. In sub-step 206c, the locking means 46 are transferred into their locking position and the instrumentation segment 18 is thus fixed on the fastening segment 16 in a torque-proof manner and fixed in position in the axial direction.

The cage positioning system 10 is thus ready for use.

In a further step 208, the cage 12 can now be introduced into the surgical site in the direction of its transverse axis 140 and introduced into the intervertebral disk compartment 142 of the spine to be supplied with the cage 12.

By here, for example, rotationally adjusting 210 the third handle 30, the manipulator prong 98 is adjusted in a further step relative to the coupling prong(s) 88 of the instrumentation section 18 in the axial direction translationally (toward the distal end), and thus the cage 12 is forced to pivot about the coupling element 92 of the coupling prong 88 or the coupling elements 98 of the coupling prongs 88 until the cage 12 is arranged in its prespecified position in the intervertebral disk compartment 142.

If the cage 12 is designed to be articulated in itself, the set angle α of the head segment 128 relative to the foot segment 126 can be set to a corresponding value by a corresponding lordosis of the spine and a corresponding deflection of the head and foot segments relative to each other. To lock 212 the set angle α, the fixing element 94 or the fixing screw is screwed into the screw-in area 138 of the cage 12 by means of the fourth handle and the first locking slide which is coupled to the movement.

In a further step, the first locking slide 34 is translationally moved back from its locking position into its releasing position in the axial direction. The second locking slide 38 is translationally moved back from its locking position into its releasing position by actuating the handle 40 arranged on the instrumentation segment 18 in the direction of the longitudinal axis 22 of the positioning instrument 14. The instrumentation section 18 is now unlocked with regard to its mechanical coupling to the cage and can be disconnected in a further step with axial pull from the cage 12 and moved out of the surgical site.

In summary, the invention relates to a surgical cage positioning system (10) for the implantological replacement of an intervertebral disk, preferably in the region of the lumbar spine of humans, having a positioning instrument (14) with a first coupling prong (88) and with a first manipulator prong (98), each provided with a coupling element (92). The manipulator prong (98) can be displaced in the axial direction relative to the coupling prong (88) by means of a handle (26, 28, 30, 32, 40); The cage positioning system comprises a cage (12) with an insertion opening (114) for the instrumentation segment (18) and with coupling means (122, 124) via which the coupling elements (92) of the instrumentation segment (18), each pivotally connected to the cage (12), can be coupled so that the cage (12) is pivotable by means of the manipulator prong (98) about an axis of rotation D defined by the coupling element (92) of the coupling prong (88) and the coupling means (122, 124) of the cage (12) relative to the longitudinal axis (22) of the positioning instrument (14). The invention also relates to a cage and a positioning instrument.

What is claimed is:

1. A surgical cage positioning system for an implantological replacement of an intervertebral disk, in an area of the lumbar spine of humans, comprising:
    a positioning instrument having an actuating segment and having an instrumentation segment which extends away from the actuating segment in a direction of a longitudinal axis of the positioning instrument;
    wherein the instrumentation segment has a first coupling prong and a first manipulator prong, each of which is provided with a coupling element, wherein the manipulator prong is displaceable in an axial direction relative to the coupling prong by means of a handle; and
    a cage to be implanted, having an insertion opening for the instrumentation segment and having a coupling means via which the coupling elements of the instrumentation segment can each be pivotally coupled to the cage;
    wherein the coupling means and the coupling elements of the positioning instrument coupled to the cage interact in such a way that the cage is pivotable relative to the longitudinal axis of the positioning instrument by means of the manipulator prong about a first axis of rotation D defined by the coupling element of the coupling prong and the coupling means of the cage;
    wherein the actuating segment and the instrumentation segment can be plugged into each other and locked against each other by means of a rocker-like locking means.

2. The cage positioning system according to claim 1, wherein the coupling means of the cage assigned to the coupling element of the manipulator prong produces a translational movement of the coupling element of the manipulator prong along a non-linear movement path B relative to the cage when the cage is pivoted, wherein the coupling means of the cage assigned to the coupling element of the manipulator prong is designed as a non-linear groove or a non-linear elongated hole.

3. The cage positioning system according to claim 1, wherein the cage can be pivoted relative to the longitudinal axis of the positioning instrument by actuation of the manipulation prong over a pivot angle $\beta$, where $0°\leq\beta\leq80°$.

4. The cage positioning system according to claim 1, wherein the positioning instrument has a first locking slide which is mounted in a longitudinally displaceable manner in or on a base body of the instrumentation segment and which can be slid relative to the coupling prong in the axial direction between a releasing position in which the coupling prong coupled to the cage can be disconnected from the cage and a locking position in which the coupling prong coupled to the cage is locked on the cage, wherein the first locking slide can be actuated by means of the handle arranged on the instrumentation segment or on the actuating segment.

5. The cage positioning system according to claim 1, wherein the instrumentation segment has a second coupling prong which is arranged running parallel to the first coupling prong, wherein a first locking slide, when in a locking position, is arranged at least in sections between the two coupling prongs and blocks the two coupling prongs from nearing each other.

6. The cage positioning system according to claim 1, wherein the positioning instrument has a second locking slide which is mounted in a longitudinally displaceable manner in or on a base body of the instrumentation segment and which can be slid relative to the manipulator prong in the axial direction between a releasing position in which the manipulator prong coupled to the cage can be disconnected from the cage and a locking position in which the manipulator prong coupled to the cage is locked on the cage.

7. The cage positioning system according to claim 1, wherein the instrumentation segment has a second manipulator prong, wherein the second manipulator prong and the first manipulator prong are synchronously displaceable in the axial direction, and wherein a second locking slide, when in a locking position, is arranged at least in sections between the two manipulator prongs and blocks the same from nearing each other.

8. The cage positioning system according to claim 1, wherein the instrumentation segment and the actuating segment are each designed as separate structural units which are detachably coupled to each other.

9. The cage positioning system according to claim 1, wherein the instrumentation segment is designed for single use and the actuating segment is designed for multiple use, wherein the actuating segment can be reversibly disassembled into its individual parts and can be autoclaved multiple times.

10. The cage positioning system according to claim 1, wherein the cage has a foot segment and a head segment which are arranged so as to be pivotable relative to each other.

11. The cage positioning system according to claim 10, wherein the foot segment and the head segment are guided on each other and connected to each other via at least one tongue and groove connection.

12. The cage positioning system according to claim 10, wherein the cage has a fixing element by which the foot segment and the head segment can be fixed in position relative to each other in their respective set angle $\alpha$, wherein the fixing element is designed as a fixing screw which can be screwed into a screw-in area of the cage, which is corrugated at least in sections.

13. The cage positioning system according to claim 12, wherein the fixing element can be actuated by means of a locking slide and is releasably connected to the same, via a predetermined breaking point or a tool profile engaging in the fixing element of the locking slide, being an Allen key, wherein the locking slide is coupled or can be coupled in a torque-proof manner to the handle of the actuating section.

14. The cage positioning system according to claim 1, wherein the actuating segment of the positioning instrument has the handle for actuating the manipulator prong, wherein the actuating segment has a display by means of which a respective pivot angle β of the cage can be read relative to the longitudinal axis of the positioning tool.

15. The cage positioning system according to claim 1, wherein each coupling prong is integrally formed on a base body of the instrumentation segment.

16. The cage positioning system according to claim 1, wherein the cage has a head segment and a foot segment which can be pivoted relative to each other about a pivot axis.

17. The cage positioning system according to claim 1, having the actuating segment and having the instrumentation segment which extends from the actuating segment in the direction of the longitudinal axis of the positioning instrument, wherein the instrumentation segment has the first coupling prong and the first manipulator prong, each of which is provided with the coupling element, wherein the manipulator prong is displaceable in the axial direction relative to the coupling prong by means of the handle, and wherein its instrumentation segment is designed for single use and its actuating segment is designed for multiple use.

\* \* \* \* \*